United States Patent
Hu et al.

(10) Patent No.: US 11,915,425 B2
(45) Date of Patent: **\*Feb. 27, 2024**

(54) SYSTEMS AND METHODS FOR ATTENUATION CORRECTION

(71) Applicant: SHANGHAI UNITED IMAGING HEALTHCARE CO., LTD., Shanghai (CN)

(72) Inventors: Lingzhi Hu, Houston, TX (US); Tuoyu Cao, Houston, TX (US); Gang Yang, Shanghai (CN); Yang Lyu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 436 days.

This patent is subject to a terminal disclaimer.

(21) Appl. No.: 17/198,205

(22) Filed: Mar. 10, 2021

(65) Prior Publication Data

US 2021/0217174 A1 Jul. 15, 2021

Related U.S. Application Data

(63) Continuation of application No. 16/235,117, filed on Dec. 28, 2018, now Pat. No. 10,949,971, which is a (Continued)

(51) Int. Cl.
*G06K 9/00* (2022.01)
*A61B 5/00* (2006.01)
(Continued)

(52) U.S. Cl.
CPC ............ *G06T 7/0016* (2013.01); *A61B 5/055* (2013.01); *A61B 5/7267* (2013.01); *A61B 6/037* (2013.01);
(Continued)

(58) Field of Classification Search
CPC ..... A61B 6/5258; A61B 6/037; A61B 6/5235; A61B 5/055; G06T 11/008; G06T 11/005;
(Continued)

(56) References Cited

U.S. PATENT DOCUMENTS 9,336,613 B2 5/2016 Blaffert et al.
9,453,922 B2 9/2016 Stodilka et al.
(Continued)

FOREIGN PATENT DOCUMENTS

CN 107638188 A 1/2018

OTHER PUBLICATIONS

Liu, Fang et al., Deep Learning MR Imaging-based Attenuation Correction for PET/MR Imaging, Radiology, 286(2): 676-684, 2018.
(Continued)

*Primary Examiner* — Atiba O Fitzpatrick
(74) *Attorney, Agent, or Firm* — METIS IP LLC

(57) ABSTRACT

A method include obtaining at least one first PET image of a subject acquired by a PET scanner and at least one first MR image of the subject acquired by an MR scanner. The method may also include obtaining a target neural network model. The target neural network model may provide a mapping relationship between PET images, MR images, and corresponding attenuation correction data, and output attenuation correction data associated with a specific PET image of the PET images. The method may further include generating first attenuation correction data corresponding to the subject using the target neural network model based on the at least one first PET image and the at least one first MR image of the subject, and determining a target PET image of the subject based on the first attenuation correction data corresponding to the subject.

20 Claims, 7 Drawing Sheets

Related U.S. Application Data continuation of application No. PCT/CN2018/111188, filed on Oct. 22, 2018.

(51) Int. Cl.
  *A61B 5/055* (2006.01)
  *A61B 6/00* (2006.01)
  *A61B 6/03* (2006.01)
  *G06T 7/00* (2017.01)
  *G06T 11/00* (2006.01)

(52) U.S. Cl.
  CPC .......... *A61B 6/5247* (2013.01); *A61B 6/5282* (2013.01); *A61B 6/563* (2013.01); *G06T 11/005* (2013.01); *G06T 11/008* (2013.01); *G06T 2207/10088* (2013.01); *G06T 2207/10104* (2013.01); *G06T 2207/20081* (2013.01); *G06T 2207/20084* (2013.01); *G06T 2207/20182* (2013.01); *G06T 2207/30096* (2013.01)

(58) Field of Classification Search
  CPC .......... G06T 5/001; G06T 2207/10104; G06T 2207/10108; G06T 2207/10088; G06T 2207/10092; G06T 2207/10096; G06T 2207/20081; G06T 2207/20084; G01R 33/481; G06K 9/6256; G06K 9/6257; G06K 9/6259; G06V 10/70; G06V 10/82; G06V 10/774–7796; G06N 3/02–126; G06N 20/00–20; G06F 18/214–2155; G06F 7/023; G06F 40/16
  See application file for complete search history.

(56) References Cited

U.S. PATENT DOCUMENTS

| | | | |
|---|---|---|---|
| 10,438,350 B2 | 10/2019 | Patil et al. | |
| 2005/0215889 A1 | 9/2005 | Patterson, II | |
| 2008/0033291 A1 | 2/2008 | Rousso et al. | |
| 2008/0135769 A1* | 6/2008 | Rosen | G01R 33/481 250/363.09 |
| 2010/0010757 A1* | 1/2010 | Schmidt | A61B 6/5247 706/15 |
| 2011/0123083 A1 | 5/2011 | Ojha et al. | |
| 2011/0317900 A1 | 12/2011 | Pal et al. | |
| 2012/0230571 A1 | 9/2012 | Schmidt | |
| 2013/0101193 A1* | 4/2013 | Ra | G06T 11/005 382/131 |
| 2013/0315459 A1 | 11/2013 | Wollenweber et al. | |
| 2014/0046171 A1 | 2/2014 | Schmidt | |
| 2014/0153806 A1 | 6/2014 | Glielmi et al. | |
| 2014/0328532 A1 | 11/2014 | Sun | |
| 2015/0065854 A1 | 3/2015 | Ahn et al. | |
| 2015/0090890 A1 | 4/2015 | Deller et al. | |
| 2015/0117733 A1 | 4/2015 | Manjeshwar et al. | |
| 2015/0310653 A1 | 10/2015 | Knoll et al. | |
| 2015/0374318 A1 | 12/2015 | Koch et al. | |
| 2016/0066874 A1* | 3/2016 | Huang | A61B 6/037 600/411 |
| 2017/0061629 A1 | 3/2017 | Zhu et al. | |
| 2017/0103287 A1 | 4/2017 | Han | |
| 2017/0164915 A1 | 6/2017 | Li et al. | |
| 2018/0025512 A1 | 1/2018 | Zhu et al. | |
| 2018/0137656 A1 | 5/2018 | Li et al. | |
| 2019/0108904 A1* | 4/2019 | Zhou | G06F 18/10 |
| 2019/0130569 A1* | 5/2019 | Liu | G06T 5/50 |
| 2019/0266728 A1* | 8/2019 | Lee | A61B 6/037 |

OTHER PUBLICATIONS

International Search Report in PCT/CN2018/111188 dated Jul. 22, 2019. 4 pages.

Written Opinion in PCT/CN2018/111188 dated Jul. 22, 2019, 4 pages.

* cited by examiner

SYSTEMS AND METHODS FOR ATTENUATION CORRECTION

CROSS-REFERENCE TO RELATED APPLICATION

This application is a Continuation of U.S. patent application Ser. No. 16/235,117 filed on Dec. 28, 2018, which is a Continuation of International Application No. PCT/CN2018/111188 filed on Oct. 22, 2018, the contents of each of which is incorporated herein by reference.

TECHNICAL FIELD

The disclosure generally relates to imaging systems, and more particularly relates to systems and methods for attenuation correction.

BACKGROUND

Nuclear medicine imaging is widely used in the diagnosis and treatment of various medical conditions based on images acquired by using radiation emission. Positron emission tomography (PET) is an exemplary nuclear medicine imaging technique. PET is used to generate images that may reflect metabolic activities of a specific organ or tissue (e.g., a tumor). Generally, a PET image may be reconstructed based on attenuation correction data to present accurate information of a specific organ or tissue in a body. With the development of multi-modality imaging technique (e.g., PET-magnetic resonance (MR) imaging technique), MR images may be used for attenuation correction of a PET image. However, an MR image cannot directly present the electron density of tissue in a body, such that an attenuation correction image associated with the PET image cannot be generated directly based on the MR image. It is desired to provide systems and methods for PET image attenuation correction based on MR images.

SUMMARY

According to an aspect of the present disclosure, a system for attenuation correction is provided. The system may include at least one storage device storing executable instructions, and at least one processor in communication with the at least one storage device. When executing the executable instructions, the at least one processor may cause the system to obtain at least one first PET image of a subject acquired by a PET scanner and at least one first MR image of the subject acquired by an MR scanner. The at least one processor may also cause the system to obtain a target neural network model that provides a mapping relationship between PET images, MR images, and corresponding attenuation correction data and outputs attenuation correction data associated with a specific PET image of the PET images. The at least one processor may further cause the system to generate first attenuation correction data corresponding to the subject using the target neural network model based on the at least one first PET image and the at least one first MR image of the subject. In some embodiments, the at least one processor may also cause the system to determine a target PET image of the subject based on the first attenuation correction data corresponding to the subject.

In some embodiments, to obtain a target neural network model, the at least one processor may be further configured to cause the system to obtain multiple groups of training data and generate the target neural network model by training a neural network model using the multiple groups of training data. Each of the multiple groups of training data may include a second PET image, a second MR image, and second attenuation correction data corresponding to a sample.

In some embodiments, the neural network model may include a convolutional neural network (CNN) model, a back propagation (BP) neural network model, a radial basis function (RBF) neural network model, a deep belief nets (DBN) neural network model, an Elman neural network model, or the like, or a combination thereof.

In some embodiments, to obtain multiple groups of training data, the at least one processor may be further configured to cause the system to obtain a CT image of the sample for each training data of a sample of the multiple groups of training data, and determine the second attenuation correction data corresponding to the sample based on a CT image of the sample.

In some embodiments, to obtain multiple groups of training data, the at least one processor may be further configured to cause the system to determine the second attenuation correction data corresponding to the sample based on the at least one of the second MR image or the second PET image for each training data of a sample of the multiple groups of training data.

In some embodiments, to generate first attenuation correction data corresponding to the subject using the target neural network model based on the at least one first PET image and the at least one first MR image of the subject, the at least one processor may be further configured to cause the system to input the at least one first PET image and the at least one first MR image to the target neural network model, and obtain the first attenuation correction data output by the target neural network model.

In some embodiments, to determine a target PET image of the subject based on the first attenuation correction data corresponding to the subject, the at least one processor may be further configured to cause the system to obtain PET projection data associated with the first PET image of the subject, and reconstruct the target PET image based on the PET projection data and the first attenuation correction data.

In some embodiments, to determine a target PET image of the subject based on the first attenuation correction data corresponding to the subject, the at least one processor may be further configured to cause the system to perform a post-processing operation on the first attenuation correction data corresponding to the subject. The post-processing operation may include an interpolation operation, a registration operation, or the like, or a combination thereof.

In some embodiments, the at least one processor may be further configured to cause the system to perform a pre-processing operation on at least one of the at least one first PET image or the at least one first MR image. The pre-processing operation may include a filtering operation, a smoothing operation, a transformation operation, a denoising operation, or the like, or a combination thereof.

According to another aspect of the present disclosure, a method for attenuation correction is provided. A method include obtaining at least one first PET image of a subject acquired by a PET scanner and at least one first MR image of the subject acquired by an MR scanner. The method may also include obtaining a target neural network model. The target neural network model may provide a mapping relationship between PET images, MR images, and corresponding attenuation correction data, and output attenuation correction data associated with a specific PET image of the PET images. The method may further include generating first attenuation correction data corresponding to the subject using the target neural network model based on the at least one first PET image and the at least one first MR image of the subject, and determining a target PET image of the subject based on the first attenuation correction data corresponding to the subject.

According to another aspect of the present disclosure, a non-transitory computer-readable medium storing at least one set of instructions may be provided. When executed by at least one processor, the at least one set of instructions may direct the at least one processor to perform a method. The method may include obtaining at least one first PET image of a subject acquired by a PET scanner and at least one first MR image of the subject acquired by an MR scanner. The method may also include obtaining a target neural network model. The target neural network model may provide a mapping relationship between PET images, MR images, and corresponding attenuation correction data, and output attenuation correction data associated with a specific PET image of the PET images. The method may further include generating first attenuation correction data corresponding to the subject using the target neural network model based on the at least one first PET image and the at least one first MR image of the subject, and determining a target PET image of the subject based on the first attenuation correction data corresponding to the subject.

According to another aspect of the present disclosure, a system for attenuation correction may be provided. The system may include an acquisition module, a model determination module, and a correction module. The acquisition module may be configured to obtain at least one first PET image of a subject acquired by a PET scanner and at least one first MR image of the subject acquired by an MR scanner. The model determination module may be configured to obtain a target neural network model. The target neural network model may provide a mapping relationship between PET images, MR images, and corresponding attenuation correction data. The target neural network model may be configured to output attenuation correction data associated with a specific PET image of the PET images. The correction module may be configured to generate first attenuation correction data corresponding to the subject using the target neural network model based on the at least one first PET image and the at least one first MR image of the subject, and determine a target PET image of the subject based on the first attenuation correction data corresponding to the subject.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

Figure 3:
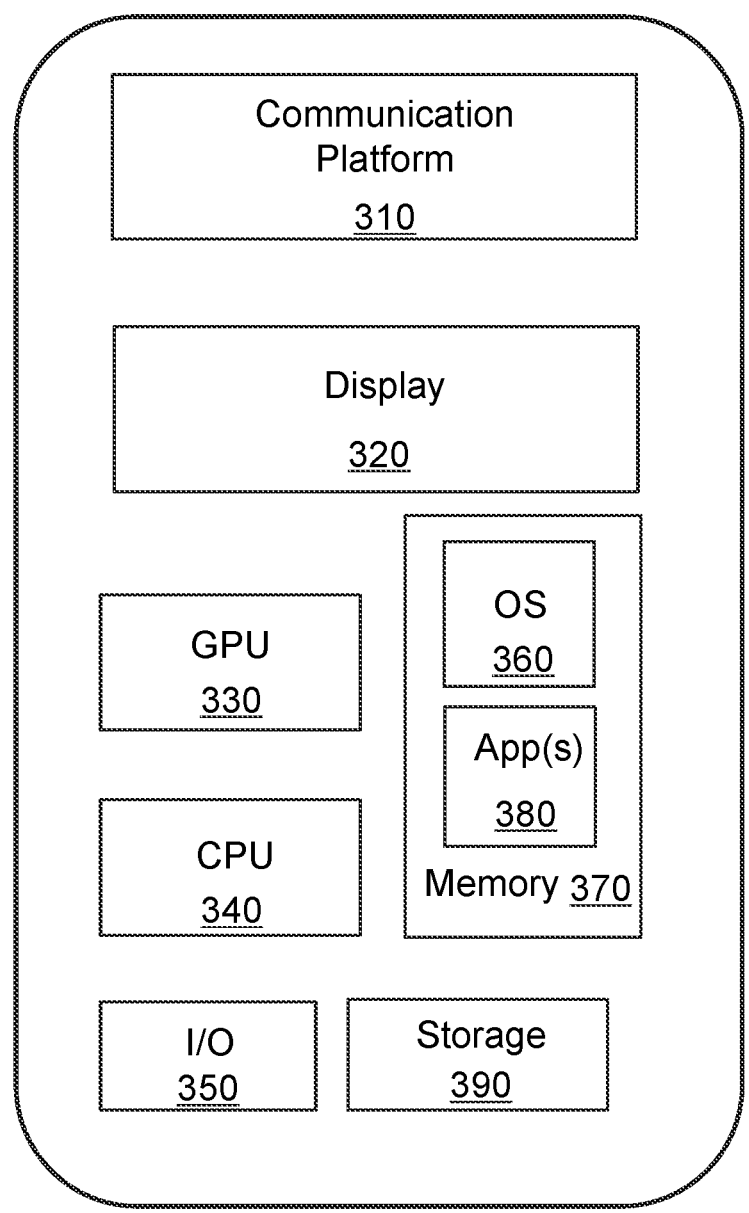
FIG. 3 is a schematic diagram illustrating hardware and/or software components of an exemplary mobile device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processing unit 320 as illustrated in FIG. 3) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for attenuation correction. A system for attenuation correction may interact with a PET scanner and an MR scanner to obtain and/or retrieve from a storage device PET image data and MR image data, respectively. The system may include at least one storage device storing executable instructions, and at least one processor in communication with the at least one storage device. When executing the executable instructions, the at least one processor may cause the system to obtain at least one first PET image of a subject (e.g., acquired by the PET scanner, retrieved from a storage device) and at least one first MR image of the subject (e.g., acquired by the MR scanner, retrieved from a storage device). The at least one processor may also cause the system to obtain a target neural network model that provides a mapping relationship between PET images, MR images, and corresponding attenuation correction data and outputs attenuation correction data associated with a specific PET image data. The at least one processor may further cause the system to generate the first attenuation correction data corresponding to the subject by inputting the at least one first PET image and the at least one first MR image of the subject in the target neural network model, and determine a target PET image of the subject based on the first attenuation correction data corresponding to the subject.

Accordingly, the system may generate attenuation correction data associated with a PET image directly by inputting the PET image and an MR image of a subject into the target neural network model, which may improve processing speed for generating the attenuation correction data and may be applied in different clinical situations. In some embodiments, the system may update a plurality of training samples according to clinical demands and update the target neural network model by training the target neural network model using the updated plurality of training samples. Accordingly, the system may adapt to complex clinical situations and have improved robustness.

Figure 1:
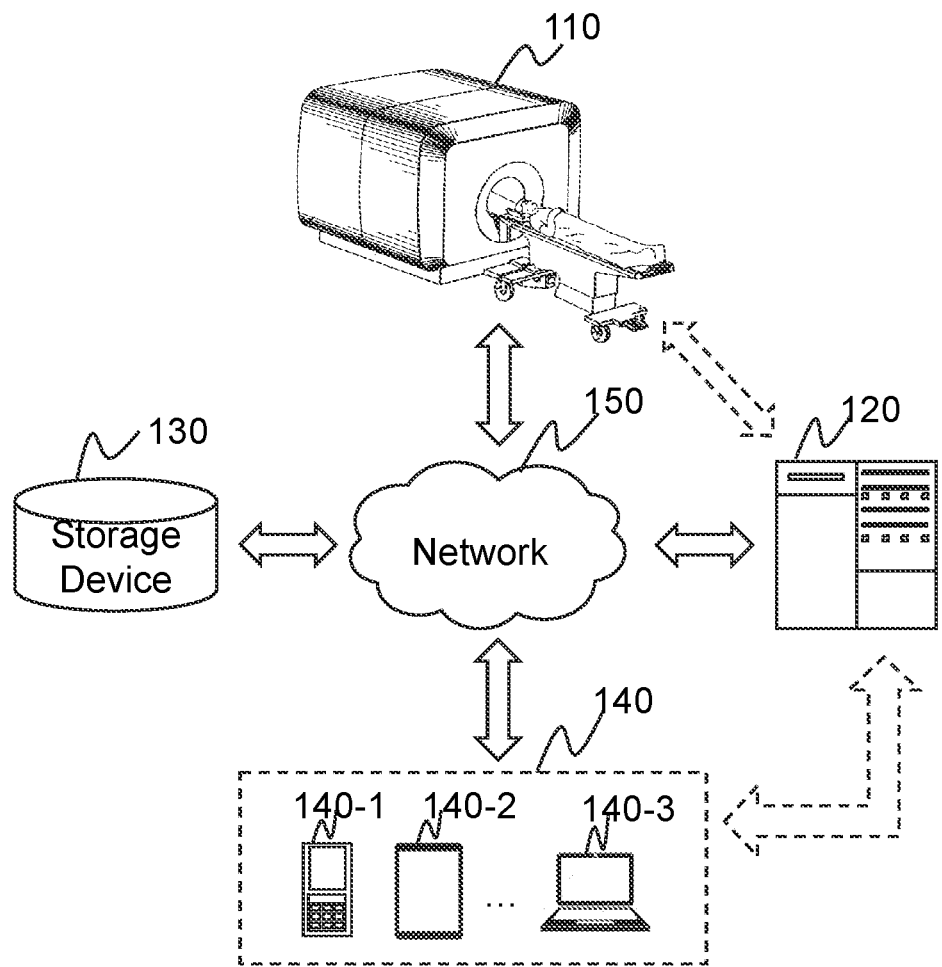
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. In some embodiments, the imaging system 100 may be a single-modality system or a multi-modality system. Exemplary single-modality systems may include a positron emission tomography (PET) system, a magnetic resonance (MR) system, etc. Exemplary multi-modality systems may include a computed tomography-positron emission tomography (CT-PET) system, a magnetic resonance-positron emission tomography (MR-PET) system, etc. In some embodiments, the imaging system 100 may include modules and/or components for performing imaging and/or related analysis.

Merely by way of example, as illustrated in FIG. 1, the imaging system 100 may include a medical device 110, a processing device 120, a storage device 130, one or more terminals 140, and a network 150. The components in the imaging system 100 may be connected in one or more of various ways. Merely by way of example, the medical device 110 may be connected to the processing device 120 through the network 150. As another example, the medical device 110 may be connected to the processing device 120 directly as illustrated in FIG. 1. As a further example, the terminal(s) 140 may be connected to another component of the imaging system 100 (e.g., the processing device 120) via the network 150. As still a further example, the terminal(s) 140 may be connected to the processing device 120 directly as illustrated by the dotted arrow in FIG. 1. As still a further example, the storage device 130 may be connected to another component of the imaging system 100 (e.g., the processing device 120) directly as illustrated in FIG. 1, or through the network 150.

The medical device 110 may include a multi-modality imaging device. The multi-modality imaging device may acquire imaging data relating to at least one part of a subject. The imaging data relating to at least one part of a subject may include an image (e.g., an image slice), projection data, or a combination thereof. In some embodiments, the imaging data may be a two-dimensional (2D) imaging data, a three-dimensional (3D) imaging data, a four-dimensional (4D) imaging data, or the like, or any combination thereof. The subject may be biological or non-biological. For example, the subject may include a patient, a man-made object, etc. As another example, the subject may include a specific portion, organ, and/or tissue of the patient. For example, the subject may include the head, the neck, the thorax, the heart, the stomach, a blood vessel, soft tissue, a tumor, nodules, or the like, or any combination thereof. Exemplary multi-modality imaging devices may include a PET-CT scanner, a PET-MR scanner, or the like, or a combination thereof. For example, the medical device 110 may include a PET scanner and an MR scanner. The PET scanner may scan a subject or a portion thereof that is located within its detection region and generate projection data relating to the subject or the portion thereof. The PET may include a gantry, a detector, an electronics module, and/or other components not shown. The gantry may support one or more parts of the PET scanner, for example, the detector, the electronics module, and/or other components. The detector may detect radiation photons (e.g., γ photons) emitted from a subject being examined. The electronics module may collect and/or process electrical signals (e.g., scintillation pulses) generated by the detector. The electronics module may convert an analog signal (e.g., an electrical signal generated by the detector) relating to a radiation photon detected by the detector to a digital signal relating to a radiation event. As used herein, a radiation event (also referred to as a single event) may refer to an interaction between a radiation photon emitted from a subject and impinging on and detected by the detector. A pair of radiation photons (e.g., γ photons) interacting with two detector blocks along a line of response (LOR) within a coincidence time window may be determined as a coincidence event. A portion of the radiation photons (e.g., γ photons) emitted from a subject being examined may interact with tissue in the subject. The radiation photons (e.g., γ photons) interacting with tissue in the subject may be scattered or otherwise change its trajectory, that may affect the number or count of radiation photons (e.g., γ photons) detected by two detector blocks along a line of response (LOR) within a coincidence time window and the number or count of coincidence events.

The MR scanner may scan a subject or a portion thereof that is located within its detection region and generate MR image data relating to the subject or the portion thereof. The MR image data may include k-space data, MR signals, an MR image, etc. The MR image data may be acquired by the MR scanner via scanning the subject using a pulse sequence. Exemplary pulse sequences may include a spin echo sequence, a gradient echo sequence, a diffusion sequence, an inversion recovery sequence, or the like, or a combination thereof. For example, the spin echo sequence may include a fast spin echo (FSE), a turbo spin echo (TSE), a rapid acquisition with relaxation enhancement (RARE), a half-Fourier acquisition single-shot turbo spin-echo (HASTE), a turbo gradient spin echo (TGSE), or the like, or a combination thereof.

The processing device 120 may process data and/or information obtained from the medical device 110, the terminal(s) 140, and/or the storage device 130. For example, the processing device 120 may obtain a PET image and an MR image relating to a subject. The processing device 120 may also obtain a target neural network model for attenuation correction. The target neural network model may provide a mapping relationship between PET images, MR images, and corresponding attenuation correction data, and output attenuation correction data associated with a specific PET image. The processing device 120 may determine the attenuation correction associated with the PET image based on the mapping relationship using the target neural network model. As another example, the processing device 120 may reconstruct a target PET image of the subject based on the attenuation correction data associated with the PET image. As still another example, the processing device 120 may obtain a plurality of training data. The processing device 120 may generate the target neural network model by training a neural network model using the plurality of training data.

In some embodiments, the processing device 120 may be a computer, a user console, a single server or a server group, etc. The server group may be centralized or distributed. In some embodiments, the processing device 120 may be local or remote. For example, the processing device 120 may access information and/or data stored in the medical device 110, the terminal(s) 140, and/or the storage device 130 via the network 150. As another example, the processing device 120 may be directly connected to the medical device 110, the terminal(s) 140 and/or the storage device 130 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage device 130 may store data, instructions, and/or any other information. In some embodiments, the storage device 130 may store data obtained from the terminal(s) 140 and/or the processing device 120. The data may include image data acquired by the processing device 120, algorithms and/or models for processing the image data, etc. For example, the storage device 130 may store image data (e.g., PET images, MR images, PET projection data, etc.) acquired by the medical device 110. As another example, the storage device 130 may store one or more algorithms for processing the image data, a target neural network model for generating attenuation data, etc. In some embodiments, the storage device 130 may store data and/or instructions that the processing device 120 may execute or use to perform exemplary methods/systems described in the present disclosure. In some embodiments, the storage device 130 may include mass storage, removable storage, volatile read-and-write memory, read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the imaging system 100 (e.g., the processing device 120, the terminal(s) 140, etc.). One or more components in the imaging system 100 may access the data or instructions stored in the storage device 130 via the network 150. In some embodiments, the storage device 130 may be directly connected to or communicate with one or more other components in the imaging system 100 (e.g., the processing device 120, the terminal(s) 140, etc.). In some embodiments, the storage device 130 may be part of the processing device 120.

The terminal(s) 140 may include a mobile device 140-1, a tablet computer 140-2, a laptop computer 140-3, or the like, or any combination thereof. In some embodiments, the mobile device 140-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 140 may be part of the processing device 120.

The network 150 may include any suitable network that can facilitate the exchange of information and/or data for the imaging system 100. In some embodiments, one or more components of the medical device 110 (e.g., a CT scanner, a PET scanner, etc.), the terminal(s) 140, the processing device 120, the storage device 130, etc., may communicate information and/or data with one or more other components of the imaging system 100 via the network 150. For example, the processing device 120 may obtain data from the medical device 110 via the network 150. As another example, the processing device 120 may obtain user instructions from the terminal(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected to the network 150 to exchange data and/or information.

It should be noted that the above description of the imaging system 100 is merely provided for the purposes of illustration, and not intended to limit the scope of the present disclosure. For persons having ordinary skills in the art, multiple variations and modifications may be made under the teachings of the present disclosure. For example, the assembly and/or function of the imaging system 100 may be varied or changed according to specific implementation scenarios.

Figure 2:
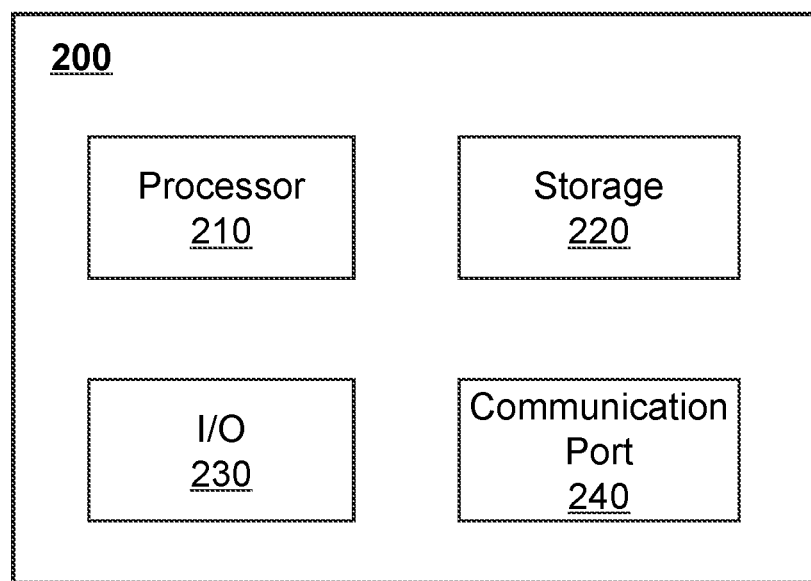
FIG. 2 is a schematic diagram illustrating hardware and/or software components of an exemplary computing device on which the processing device 120 may be implemented according to some embodiments of the present disclosure.

FIG. 2 is a schematic diagram illustrating hardware and/or software components of an exemplary computing device 200 on which the processing device 120 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program code) and perform functions of the processing device 120 in accordance with techniques described herein. The computer instructions may include, for example, routines, programs, objects, components, signals, data structures, procedures, modules, and functions, which perform particular functions described herein. For example, the processor 210 may process data obtained from the medical device 110, the terminal(s) 140, the storage device 130, and/or any other component of the imaging system 100. Specifically, the processor 210 may process one or more measured data sets obtained from the medical device 110. For example, the processor 210 may reconstruct an image based on the data set(s). In some embodiments, the reconstructed image may be stored in the storage device 130, the storage 220, etc. In some embodiments, the reconstructed image may be displayed on a display device by the I/O 230. In some embodiments, the processor 210 may perform instructions obtained from the terminal(s) 140. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the medical device 110, the terminal(s) 140, the storage device 130, or any other component of the imaging system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 120 for generating attenuation correction data for a PET image.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 150) to facilitate data communications. The communication port 240 may establish connections between the processing device 120 and the medical device 110, the terminal(s) 140, or the storage device 130. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating hardware and/or software components of an exemplary mobile device 300 according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 120. User interactions with the information stream may be achieved via the I/O 350 and provided to the processing device 120 and/or other components of the imaging system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an image as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
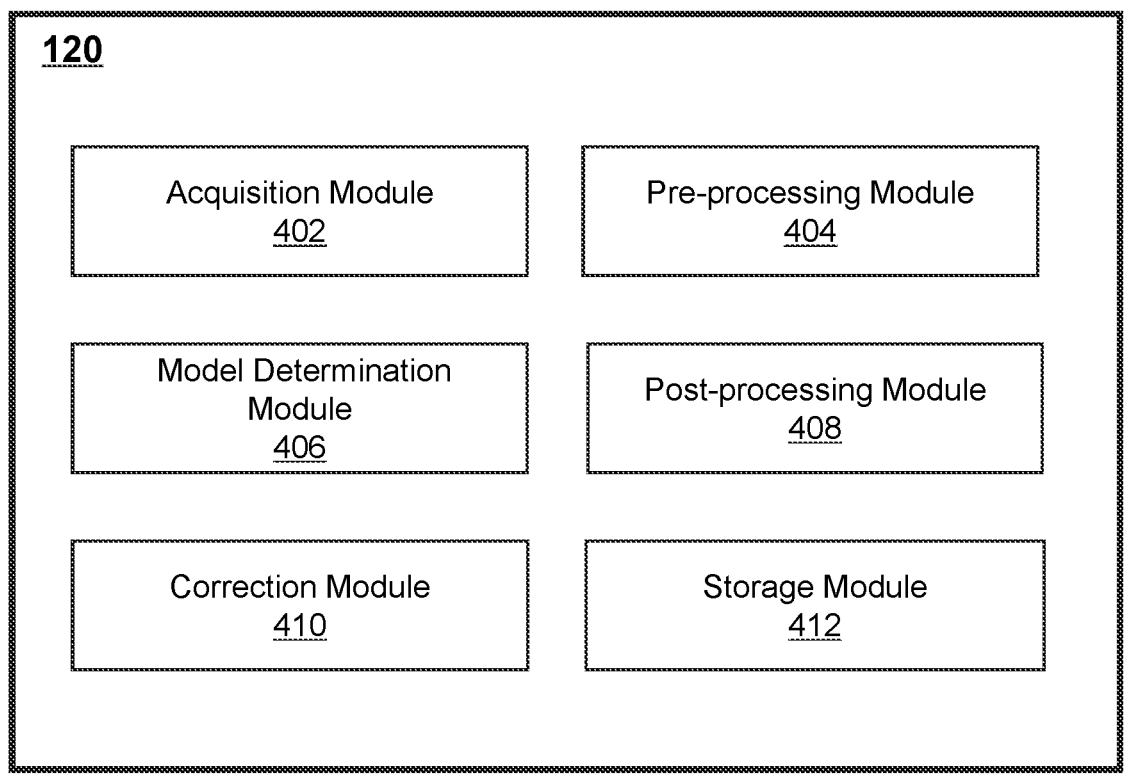
FIG. 4 is a block diagram illustrating an exemplary processing device according to some embodiments of the present disclosure.

FIG. 4 is a block diagram illustrating an exemplary processing device 120 according to some embodiments of the present disclosure. In some embodiments, the processing device 120 may be implemented on a computing device as illustrated in FIG. 2 or a mobile device as illustrated in FIG. 3. As illustrated in FIG. 4, the processing device 120 may include an acquisition module 402, a pre-processing module 404, a model determination module 406, a post-processing module 408, a correction module 410, and a storage module 412. In some embodiments, the modules may be connected with each other via a wired connection (e.g., a metal cable, an optical cable, a hybrid cable, or the like, or any combination thereof) or a wireless connection (e.g., a Local Area Network (LAN), a Wide Area Network (WAN), a Bluetooth, a ZigBee, a Near Field Communication (NFC), or the like, or a combination thereof).

The acquisition module 402 may be configured to obtain information and/or data for attenuation correction. In some embodiments, the acquisition module 402 may be configured to obtain one or more PET images and one or more MR images relating to one or more subjects. In some embodiments, the acquisition module 402 may be configured to obtain a target neural network model that provides a mapping relationship between PET images, MR images, and corresponding attenuation correction data, and output attenuation correction data associated with a specific PET image. The acquisition module 402 may transmit the information and/or data for attenuation correction to other components of the processing device 120 for further processing. For example, the acquisition module 402 may transmit a PET image, an MR image, and a target neural network model to the correction module 410 to determine attenuation correction data associated with the PET image.

The pre-processing module 404 may be configured to perform one or more pre-processing operations on an image. The image may include a PET image, an MR image, or the like, or a combination thereof. The pre-processing operation may be performed to adjust the quality of an image (e.g., a PET image, an MR image, etc.), such as the noise level of an image, the contrast ratio of an image, etc. In some embodiments, the pre-processing operation may include a denoising operation, an enhancement operation, a smoothing operation, a fusion operation, a segmentation operation, a registration operation, a transformation operation, or the like, or a combination thereof. The pre-processing module 404 may transmit the pre-processed image to other components of the processing device 120 for further processing. For example, the pre-processing module 404 may transmit a pre-processed PET image and/or pre-processed MR image to the correction module 410 to determine attenuation correction data associated with the PET image.

The model determination module 406 may be configured to generate a target neural network model for attenuation correction. The target neural network model may provide a mapping relationship between PET images, MR images, and corresponding attenuation correction data. The target neural network model may be configured to output attenuation correction data associated with a specific PET image when the specific PET image and a corresponding MR image are inputted into the target neural network model based on the mapping relationship. The target neural network model may be constructed based on a neural network model. Exemplary neural network models may include a back propagation (BP) neural network model, a radial basis function (RBF) neural network model, a deep belief nets (DBN) neural network model, an Elman neural network model, or the like, or a combination thereof. In some embodiments, the model determination module 406 may generate the target neural network model by training the neural network model using a plurality of groups of training data relating to multiple samples. Each of the plurality of groups of training data may include a PET image, an MR image, and attenuation correction data corresponding to a sample. The model determination module 406 may transmit the target neural network model to other components of the processing device 120 for further processing. For example, the model determination module 406 may transmit the target neural network model to the correction module 410 to determine attenuation correction data associated with a PET image.

The post-processing module 408 may be configured to perform a post-processing on attenuation correction data associated with a PET image. In some embodiments, the post-processing operation may include an interpolation operation, a registration operation, a transformation operation, or the like, or a combination thereof. The interpolation operation may be performed using, for example, a nearest neighbor interpolation algorithm, a bilinear interpolation algorithm, a double square interpolation algorithm, a bicubic interpolation algorithm, or the like, or a combination thereof. The registration operation may be performed using, for example, a cross-correlation algorithm, a Walsh transform algorithm, a phase correlation algorithm, etc. The post-processing module 408 may transmit the post-processed attenuation correction data to other components of the processing device 120 for further processing. For example, the post-processing module 408 may transmit the post-processed attenuation correction data to the correction module 410 to correct a PET image.

The correction module 410 may be configured to generate attenuation correction data associated with a PET image, correct the PET image, and/or generate a target PET image relating to a subject based on the attenuation correction data associated with the PET image. In some embodiments, the attenuation correction data associated with the PET image may be generated by inputting the PET image and a corresponding MR image into the target neural network model. The target neural network model may determine the attenuation correction data associated with the PET image based on the mapping relationship. Then the target neural network model may be configured to output the attenuation correction data associated with the PET image.

In some embodiments, the target PET image may be reconstructed based on PET projection data (e.g., sonogram data) and the attenuation correction data associated with the PET image using a PET image reconstruction technique as described elsewhere in the present disclosure. In some embodiments, the target PET image may be generated by correcting the PET image based on the attenuation correction data associated with the PET image. The correction module 410 may transmit the target PET image relating to a subject to other components of the imaging system 100. For example, the correction module 410 may transmit the target PET image to the terminal(s) 140 for display or the storage device 130 for store.

The storage module 412 may store information. The information may include programs, software, algorithms, data, text, number, images and some other information. For example, the information may include a PET image, an MR image, attenuation correction data associated with the PET image, etc.

It should be noted that the above description of the processing device 120 is merely provided for the purposes of illustration, and not intended to limit the scope of the present disclosure. For persons having ordinary skills in the art, multiple variations and modifications may be made under the teachings of the present disclosure. For instance, the assembly and/or function of the processing device 120 may be varied or changed according to specific implementation scenarios. Merely by way of example, the pre-processing module 404 and the post-processing module 408 may be integrated into a single module. As another example, some other components/modules may be added into the processing device 120. Such variations and modifications do not depart from the scope of the present disclosure.

Figure 5:
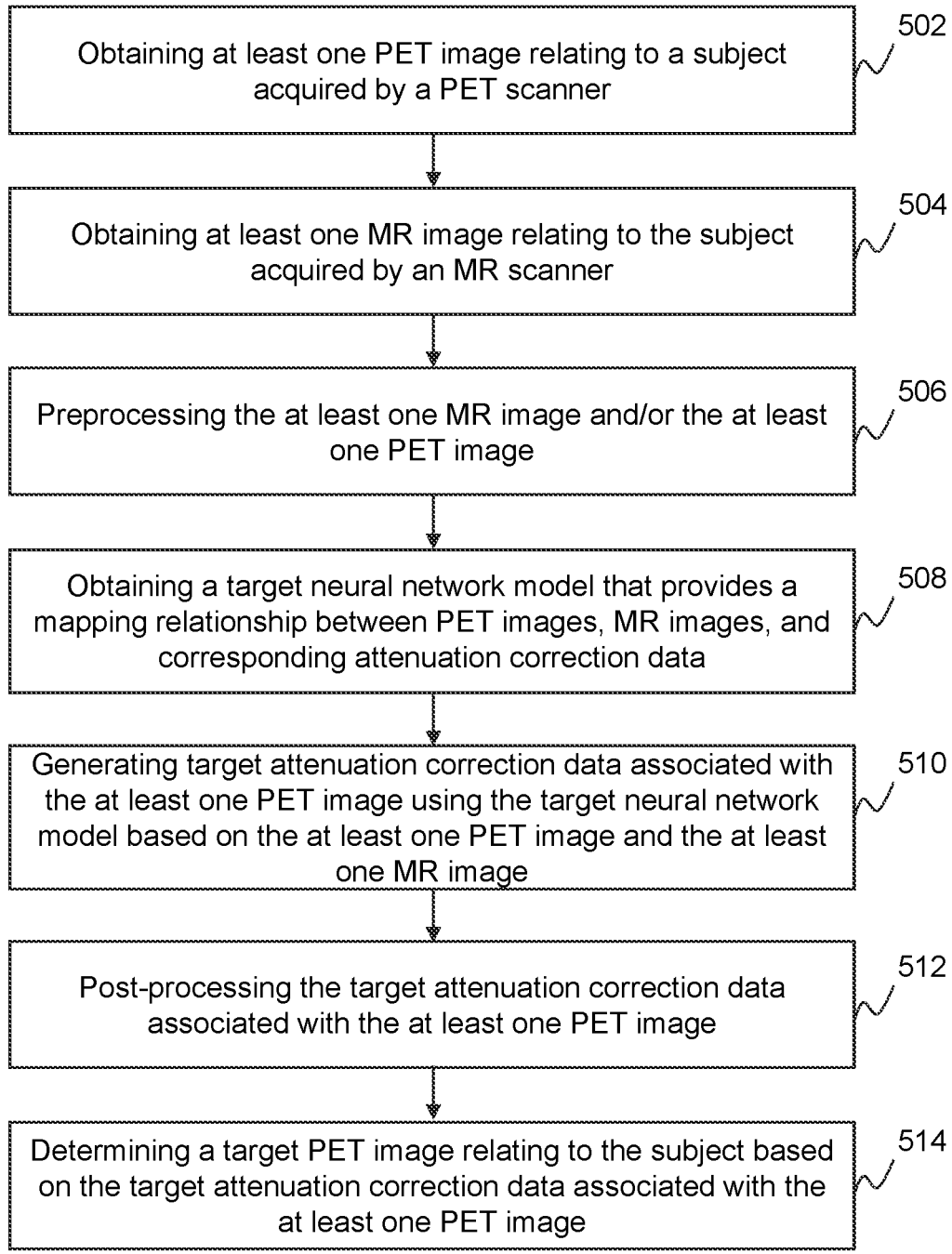
FIG. 5 is a flowchart illustrating an exemplary process for attenuation correction for PET imaging according to some embodiments of the present disclosure.

FIG. 5 is a flowchart illustrating an exemplary process 500 of attenuation correction for PET imaging according to some embodiments of the present disclosure. In some embodiments, one or more operations of the process 500 illustrated in FIG. 5 may be implemented in the imaging system 100 illustrated in FIG. 1. For example, process 500 illustrated in FIG. 5 may be stored in the storage device 130 in the form of instructions, and invoked and/or executed by the processing device 120 (e.g., the processor 210 of the computing device 200 as illustrated in FIG. 2, the GPU 330 or CPU 340 of the mobile device 300 as illustrated in FIG. 3).

In 502, at least one PET image of a subject may be obtained. Operation 502 may be performed by the acquisition module 402. In some embodiments, the at least one PET image (also referred to as at least one first PET image) may be acquired by a PET scanner, such as a PET scanner of a multi-modality imaging device (e.g., a PET scanner of the medical device 110). The acquisition module 402 may obtain the at least one PET image of the subject from the PET scanner, the storage device 130, the storage 220, the storage 390, or any other storage device. In some embodiments, the at least one PET image of the subject may be reconstructed based on PET projection data of the subject using a PET image reconstruction technique. The PET projection data (e.g., sonogram data) may be acquired by the PET scanner via scanning the subject. Exemplary PET image reconstruction techniques may include an iterative reconstruction algorithm, a Fourier slice theorem algorithm, a filtered back projection (FBP) algorithm, a fan-beam reconstruction algorithm, an analytic reconstruction algorithm, or the like, or any combination thereof. Exemplary iterative reconstruction algorithms may include a statistical reconstruction algorithm, a maximum likelihood expectation maximum algorithm, a conjugate gradient (CG) algorithm, a maximum a posteriori (MAP) algorithm, etc. The at least one PET image may include a two dimensional (2D)

PET image, a three dimensional (3D) PET image, a fourth dimensional (4D) PET image, etc.

In 504, at least one MR image of the subject may be obtained. Operation 504 may be performed by the acquisition module 402. In some embodiments, the at least one MR image (also referred to as at least one first MR image) may be acquired by an MR scanner, such as an MR scanner of the multi-modality imaging device (e.g., an MR scanner of the medical device 110). The acquisition module 402 may obtain the at least one MR image of the subject from the MR scanner, the storage device 130, the storage 220, the storage 390, or any other storage device. In some embodiments, the at least one MR image of the subject may be reconstructed based on scan data relating to the subject using an MR image reconstruction technique. Exemplary MR image reconstruction techniques may include a 2-dimensional Fourier transform technique, a back projection technique (e.g., a convolution back projection technique, a filtered back projection technique), an iteration technique, etc. Exemplary iteration techniques may include an algebraic reconstruction technique (ART), a simultaneous iterative reconstruction technique (SIRT), a simultaneous algebraic reconstruction technique (SART), an adaptive statistical iterative reconstruction (ASIR) technique, a model-based iterative reconstruction (MBIR) technique, a sinogram affirmed iterative reconstruction (SAFIR) technique, or the like, or any combination thereof. The at least one MR image reconstructed based on the scan data may include a gradient echo MR image, a spin echo MR image, or the like, or a combination thereof. The at least one MR image may include a two dimensional (2D) MR image, a three dimensional (3D) MR image, a fourth dimensional (4D) MR image, etc.

In 506, the at least one PET image and/or the at least one MR image may be pre-processed. Operation 506 may be performed by the pre-processing module 404. The pre-processing operation may be performed to adjust the quality of an image (e.g., the at least one PET image, the at least one MR image, etc.), such as the noise level of an image, the contrast of an image, the artifact of an image, the resolution of an image, etc. In some embodiments, the pre-processing operation may include a denoising operation, an enhancement operation, a smoothing operation, a fusion operation, a segmentation operation, a registration operation, a transformation operation, or the like, or a combination thereof. Specifically, the smoothing operation may be performed based on a Gaussian filter, an average filter, a median filter, a wavelet transformation, or the like, or a combination thereof. The enhancement operation may include a histogram equalization, an image sharpening, a Fourier transform, a high-pass filtering, a low-pass filtering, or the like, or a combination thereof. The denoising operation may include applying a spatial-domain filter, a transform-domain filter, a morphological noise filter, or the like, or a combination thereof. The segmentation operation may be performed based on a segmentation algorithm. Exemplary segmentation algorithms may include a threshold-based segmentation algorithm, an edge-based segmentation algorithm, a region-based segmentation algorithm, or the like, or a combination thereof. The fusion operation may be performed using, for example, an optimal seam-line algorithm, a gradient pyramid algorithm, etc. The registration operation may be performed using, for example, a cross-correlation algorithm, a Walsh transform algorithm, a phase correlation algorithm, etc. The transformation operation may include an image geometric transformation, an image perspective transformation, an image affine transformation, etc.

In 508, a target neural network model that provides a mapping relationship between PET images, MR images, and corresponding attenuation correction data may be obtained. Operation 508 may be performed by the acquisition module 402 and/or the model determination module 406. The target neural network model may be configured to output attenuation correction data associated with a specific PET image when the specific PET image and a corresponding MR image are inputted into the target neural network model based on the mapping relationship. In some embodiments, the acquisition module 402 may obtain the target neural network model from the storage device 130, the storage 220, the storage 390, the storage module 412, or any other storage device. In some embodiments, the model determination module 406 may generate the target neural network model by training a neural network model using a plurality of groups of training data relating to multiple samples. Exemplary neural network models may include a back propagation (BP) neural network model, a radial basis function (RBF) neural network model, a deep belief nets (DBN) neural network model, an Elman neural network model, or the like, or a combination thereof. Each of the plurality of groups of training data may include a PET image (also referred to as a second PET image), an MR image (also referred to as a second MR image), and reference attenuation correction data (also referred to as second attenuation correction data) corresponding to a sample. During a training process of the neural network model, the mapping relationship between a PET image, an MR image, and attenuation correction data associated with the PET image may be established based on the plurality of groups of training samples, and the trained neural network model may be determined as the target neural network model. More descriptions for generating a target neural network model may be found elsewhere in the present disclosure (e.g., FIG. 6 and FIG. 7, and the descriptions thereof).

In 510, target attenuation correction data associated with the at least one PET image may be generated based on the at least one PET image and the at least one MR image using the target neural network model. Operation 510 may be performed by the correction module 410. In some embodiments, the target attenuation correction data (also referred to as first attenuation correction data) associated with the at least one PET image may be generated by inputting the at least one PET image (the at least one PET image obtained in 502 or the at least one pre-processed PET image in 506) and the at least one MR image (the at least one MR image obtained in 504 or the at least one pre-processed MR image in 506) into the target neural network model. The target neural network model may determine the target attenuation correction data associated with the at least one PET image based on the mapping relationship. Then the target neural network model may be configured to output the target attenuation correction data associated with the at least one PET image.

The target attenuation correction data associated with the at least one PET image may present the distribution of attenuation coefficients relating to various portions or compositions of the subject. The target attenuation correction data may be in form of an image, a matrix, a mask, etc. In some embodiments, the target attenuation correction data associated with the at least one PET image may include an attenuation correction image corresponding to the subject. The attenuation correction image corresponding to the subject may include a 2D attenuation correction image, a 3D attenuation correction image, etc. The attenuation correction image corresponding to the subject may present the subject based on a plurality of pixels or voxels. The attenuation coefficients relating to various portions or compositions of the subject may be denoted by the values of the plurality of pixels or voxels in the attenuation correction image. In some embodiments, the target attenuation correction data associated with the at least one PET image may be denoted by a matrix (e.g., a 2D matrix, a 3D matrix, etc.) including a plurality of elements. One of the plurality of elements may denote an attenuation coefficient associated with at least one portion of the subject.

In 512, the target attenuation correction data associated with the at least one PET image may be post-processed. Operation 512 may be performed by the post-processing module 408. In some embodiments, the post-processing operation may include an interpolation operation, a registration operation, a transformation operation, or the like, or a combination thereof. The interpolation operation may be performed using, for example, a nearest neighbor interpolation algorithm, a bilinear interpolation algorithm, a double square interpolation algorithm, a bicubic interpolation algorithm, or the like, or a combination thereof. The interpolation operation performed on the target attenuation correction data may adjust the resolution of the target attenuation correction data (e.g., an attenuation correction image) associated with the at least one PET image. For example, the at least one PET image may be expressed in the form of a first matrix including a plurality of first elements. The target attenuation correction data associated with the at least one PET image may be expressed in the form of a second matrix including a plurality of second elements. One of the plurality of second elements may correspond to one or more of the plurality of first elements. The interpolation operation performed on the target attenuation correction data may cause each of the plurality of second elements of the target attenuation correction data to correspond to one single first element in the at least one PET image.

The registration operation may be performed using, for example, a cross-correlation algorithm, a Walsh transform algorithm, a phase correlation algorithm, etc. The registration operation may be performed between the at least one PET image and the target attenuation correction data to match an element of the at least one PET image with a corresponding element of the target attenuation correction data. As used herein, an element of the at least one PET image may be considered corresponding to an element of the target attenuation correction data if the element of the at least one PET image and the element of the attenuation correction data correspond to a same spatial position or portion of the subject. For example, the registration operation may be performed to match an element of the attenuation correction data with a corresponding element of the at least one PET image. The element of the attenuation correction data and the corresponding element of the attenuation correction data may correspond to a same spatial position or portion of the subject.

In 514, a target PET image relating to the subject may be determined based on the target attenuation correction data associated with the at least one PET image. Operation 514 may be performed by the correction module 410. In some embodiments, the target PET image may be reconstructed based on PET projection data (e.g., sonogram data) associated with the at least one PET image and the target attenuation correction data (the attenuation correction data generated in 510 or the post-processed attenuation correction data in 512) using a PET image reconstruction technique as described elsewhere in the present disclosure. For example, the target attenuation correction data (e.g., an attenuation correction image) may be projected to generate projected attenuation data using a projection transformation technique (e.g., a Radon transform). The target PET image may be reconstructed based on the projected attenuation data and the PET projection data (e.g., sonogram data) relating to the subject using a PET image reconstruction technique as described elsewhere in the present disclosure. The PET projection data associated with the at least one PET image may be obtained from the PET scanner, the storage device 130, the storage 220, the storage 390, or any other storage device.

In some embodiments, the target PET image may be generated by correcting the at least one PET image based on the target attenuation correction data associated with the at least one PET image. For example, the at least one PET image may be expressed in the form of a first matrix including a plurality of first elements. The target attenuation correction data associated with the at least one PET image may be expressed in the form of a second matrix including a plurality of second elements. One of the plurality of second elements may correspond to one or more of the plurality of first elements. The target PET image may be generated by multiplying each of the plurality of first elements with a corresponding second element.

Accordingly, the system may generate attenuation correction data associated with a PET image directly by inputting the PET image and an MR image of a subject into the target neural network model, which may improve processing speed for generating the attenuation correction data and may be applied in different clinical situations.

It should be noted that the above description of the process of attenuation correction for PET imaging is merely provided for the purposes of illustration, and not intended to limit the scope of the present disclosure. For persons having ordinary skills in the art, multiple variations and modifications may be made under the teachings of the present disclosure. For example, operation 502 and operation 504 may be performed simultaneously. As another example, process 500 may further include storing the at least one PET image, the at least one MR image, and the target attenuation data associated with the at least one PET image. The at least one PET image, the at least one MR image, and the target attenuation data associated with the at least one PET image may be used to update a training set of the target neural network model. Process 500 may further include updating the target neural network model based on the updated training set. As still a further example, operation 506 and/or operation 512 may be omitted. Such variations and modifications do not depart from the scope of the present disclosure.

Figure 6:
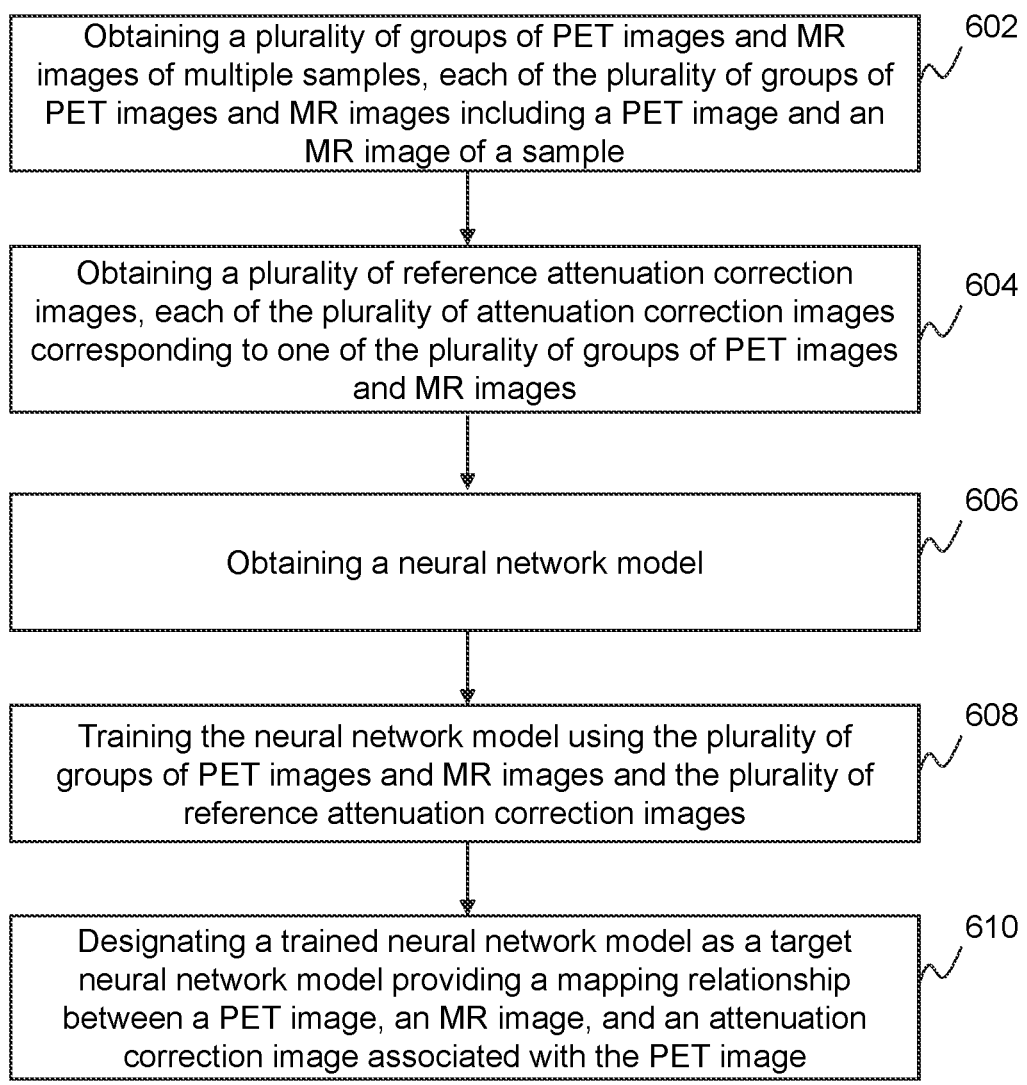
FIG. 6 is a flowchart illustrating an exemplary process for generating a target neural network model for attenuation correction according to some embodiments of the present disclosure.

FIG. 6 is a flowchart illustrating an exemplary process 600 of generating a target neural network model for attenuation correction according to some embodiments of the present disclosure. In some embodiments, one or more operations of the process 600 illustrated in FIG. 6 may be implemented in the imaging system 100 illustrated in FIG. 1. For example, the process 600 illustrated in FIG. 6 may be stored in the storage device 130 in the form of instructions, and invoked and/or executed by the processing device 120 (e.g., the processor 210 of the computing device 200 as illustrated in FIG. 2, the GPU 330 or CPU 340 of the mobile device 300 as illustrated in FIG. 3).

In 602, a plurality of groups of PET images and MR images of multiple samples may be obtained. Operation 602 may be performed by the acquisition module 402 and/or the model determination module 406. Each of the plurality of groups of PET images and MR images may include a PET image and an MR image of a sample. A sample may include a subject as described elsewhere in the present disclosure (e.g., FIG. 1 and the descriptions thereof) or not. In some embodiments, the PET image (also referred to as a second PET image) and the MR image (also referred to as a second MR image) may be acquired by a PET scanner and an MR scanner, respectively, such as a PET scanner and an MR scanner of a multi-modality imaging device (e.g., the medical device 110). The acquisition module 402 may obtain the plurality of groups of PET images and MR images from the medical device 110, the storage device 130, the storage 220, the storage 390, or any other storage device.

In 604, a plurality of reference attenuation correction images may be obtained. Operation 604 may be performed by the acquisition module 402 and/or the model determination module 406. Each of the plurality of reference attenuation correction images may correspond to one group of the plurality of groups of PET images and MR images of a sample. In some embodiments, a reference attenuation correction image (also referred to as third attenuation correction image) associated with a PET image and an MR image of a sample may be generated based on a CT image of the sample. In some embodiments, the CT image may be acquired by a CT scanner, such as a CT scanner of a multi-modality imaging device (e.g., a PET-CT scanner) via scanning the sample. In some embodiments, the CT image of a sample may be transformed into the reference attenuation correction image associated with a PET image of the sample using for example, a scaling technique, an image segmentation technique, a Hybrid technique, a bilinear technique, a dual-energy X-ray CT technique, etc. For example, using the scaling technique, the reference attenuation correction image associated with the PET image of the sample may be determined by multiplying a ratio and pixel values of the CT image. As another example, using the image segmentation technique, the sample presented in the CT image may be identified and classified into various portions (e.g., water, adipose tissues, bone tissues, lung, etc.). The various portions may be designated with various attenuation coefficients (or values) according to clinical experience by a user or according to a default setting of the imaging system 100. The reference attenuation correction image associated with the PET image may be determined based on the various attenuation coefficients (or values) corresponding to various portions (e.g., water, adipose tissues, bone tissues, lungs, etc.) of the sample.

In some embodiments, a reference attenuation correction image associated with a PET image of a sample may be generated based on at least one of the PET image and the MR image. For example, the reference attenuation correction image associated with the PET image and the MR image may be generated using a segmentation technique. Specifically, the sample presented in the MR image and/or the PET image may be identified and classified into different portions (e.g., water, adipose tissues, bone tissues, lungs, etc.). The various portions presented in the PET image and the MR image may be fused and assigned various attenuation coefficients (or values) according to clinical experience by a user or according to a default setting of the imaging system 100. The reference attenuation correction image associated with the PET image and the MR image may be determined based on the various attenuation coefficients (or values) corresponding to various portions (e.g., water, adipose tissue, bone tissue, lungs, etc.) of the subject. As another example, the attenuation correction image associated with the PET image and the MR image may be generated using a body map technique. Using the body map technique, the MR image may be registered with a reference body map including various attenuation coefficients (or values) corresponding to different tissues or organs. The reference attenuation correction image associated with the PET image may be generated based on the registration.

In 606, a neural network model may be obtained. Operation 606 may be performed by the acquisition module 402 and/or the model determination module 406. Exemplary neural network models may include a back propagation (BP) neural network model, a radial basis function (RBF) neural network model, a deep belief nets (DBN) neural network model, an Elman neural network model, or the like, or a combination thereof. In some embodiments, the neural network model may include multiple layers, for example, an input layer, multiple hidden layers, and an output layer. The multiple hidden layers may include one or more convolutional layers, one or more batch normalization layers, one or more activation layers, a fully connected layer, a cost function layer, etc. Each of the multiple layers may include a plurality of nodes.

In some embodiments, the neural network model may be defined by a plurality of parameters. Exemplary parameters of the neural network model may include the size of a convolutional kernel, the number of layers, the number of nodes in each layer, a connected weight between two connected nodes, a bias vector relating to a node, etc. The connected weight between two connected nodes may be configured to represent a proportion of an output value of a node to be as an input value of another connected node. The bias vector relating to a node may be configured to control an output value of the node deviating from an origin.

In 608, the neural network model may be trained using the plurality of groups of PET images and MR images, and the multiple attenuation correction data. Operation 608 may be performed by the model determination module 406. Exemplary neural network training algorithm may include a gradient descent algorithm, a Newton's algorithm, a Quasi-Newton algorithm, a Levenberg-Marquardt algorithm, a conjugate gradient algorithm, or the like, or a combination thereof, as exemplified in FIG. 7 and the description thereof. In some embodiments, the neural network model may be trained by performing a plurality of iterations. Before the plurality of iterations, the parameters of the neural network model may be initialized. For example, the connected weights and/or the bias vector of nodes of the neural network model may be initialized to be random values in a range, e.g., the range from −1 to 1. As another example, all the connected weights of the neural network model may have a same value in the range from −1 to 1, for example, 0. As still an example, the bias vector of nodes in the neural network model may be initialized to be random values in a range from 0 to 1. In some embodiments, the parameters of the neural network model may be initialized based on a Gaussian random algorithm, a Xavier algorithm, etc. Then the plurality of iterations may be performed to update the parameters of the neural network model until a condition is satisfied. The condition may provide an indication of whether the neural network model is sufficiently trained. For example, the condition may be satisfied if the value of a cost function associated with the neural network model is minimal or smaller than a threshold (e.g., a constant). As another example, the condition may be satisfied if the value of the cost function converges. The convergence may be deemed to have occurred if the variation of the values of the cost function in two or more consecutive iterations is smaller than a threshold (e.g., a constant). As still an example, the condition may be satisfied when a specified number of iterations are performed in the training process.

For each of the plurality of iterations, a PET image and an MR image in one group of the plurality of groups of PET images and MR images and the corresponding reference attenuation correction image may be inputted into the neural network model. The PET image and the MR image may be processed by one or more layers of the neural network model to generate an estimated attenuation correction image. The estimated attenuation correction image may be compared with the reference attenuation correction image associated with the PET image based on the cost function of the neural network model. The cost function of the neural network model may be configured to assess a difference between a testing value (e.g., the estimated attenuation correction image) of the neural network model and a desired value (e.g., the reference attenuation correction image associated with the PET image). If the value of the cost function exceeds a threshold in a current iteration, the parameters of the neural network model may be adjusted and updated to cause the value of the cost function corresponding to the PET image and the MR image (i.e., the difference between the estimated attenuation correction image and the reference attenuation correction image) smaller than the threshold. Accordingly, in a next iteration, another group of a PET image and an MR image, and a corresponding reference attenuation correction image may be inputted into the neural network model to train the neural network model as described above until the condition is satisfied.

In 610, a trained neural network model may be determined as a target neural network model that provides a mapping relationship between PET images, MR images, and corresponding attenuation correction images. Operation 610 may be performed by the model determination module 406. The trained neural network model may be configured to output an attenuation correction image associated with a specific PET image based on the mapping relationship when the specific PET image and a corresponding MR image are inputted into the trained neural network model. In some embodiments, the trained neural network model may be determined based on the updated parameters. In some embodiments, the target neural network model may be transmitted to the storage device 130, the storage module 412, or any other storage device for storage.

In some embodiments, the target neural network model may be updated based on a testing performed on the target neural network model. If the test result of the target neural network model does not satisfy a condition, the target neural network model may be updated. The target neural network model may be tested based on one or more groups of test data. A group of test samples may include a test PET image, a test MR image, and a reference attenuation correction image associated with the test PET image. A test PET image and a test MR image may be inputted into the target neural network model to output a predicted attenuation correction image associated with the test PET image. The predicted attenuation correction image associated with the test PET image may be compared with the reference attenuation correction image associated with the test PET image. If the difference between the predicted attenuation correction image and the reference attenuation correction image associated with the test PET image is greater than a threshold, the test result of the target neural network model is deemed not satisfying the condition, and the target neural network model may need to be updated. The testing of the target neural network model may be performed according to an instruction of a user, clinical demands, or a default setting of the imaging system 100. For example, the target neural network model may be tested at set intervals (e.g., every other month, every two months, etc.). As another example, the target neural network model may be updated based on added data in a training set of the target neural network model over a period of time. If the quantity of the added data in the training set over a period of time is greater than a threshold, the target neural network model may be updated based on the updated training set. Accordingly, the target neural network model may adapt to a complex clinical situation and have improved robustness.

It should be noted that the above description of the process of allocating computing resources for medical applications in response to requests for performing the medical applications is merely provided for the purposes of illustration, and not intended to limit the scope of the present disclosure. For persons having ordinary skills in the art, multiple variations and modifications may be made under the teachings of the present disclosure. Such variations and modifications do not depart from the scope of the present disclosure. For example, operation 602 and operation 604 may be performed simultaneously. As another example, operation 610 may be omitted. In some embodiments, the convergence may be deemed to have occurred if the variation of the values of the cost function in two or more consecutive iterations is equal to a threshold (e.g., a constant).

Figure 7:
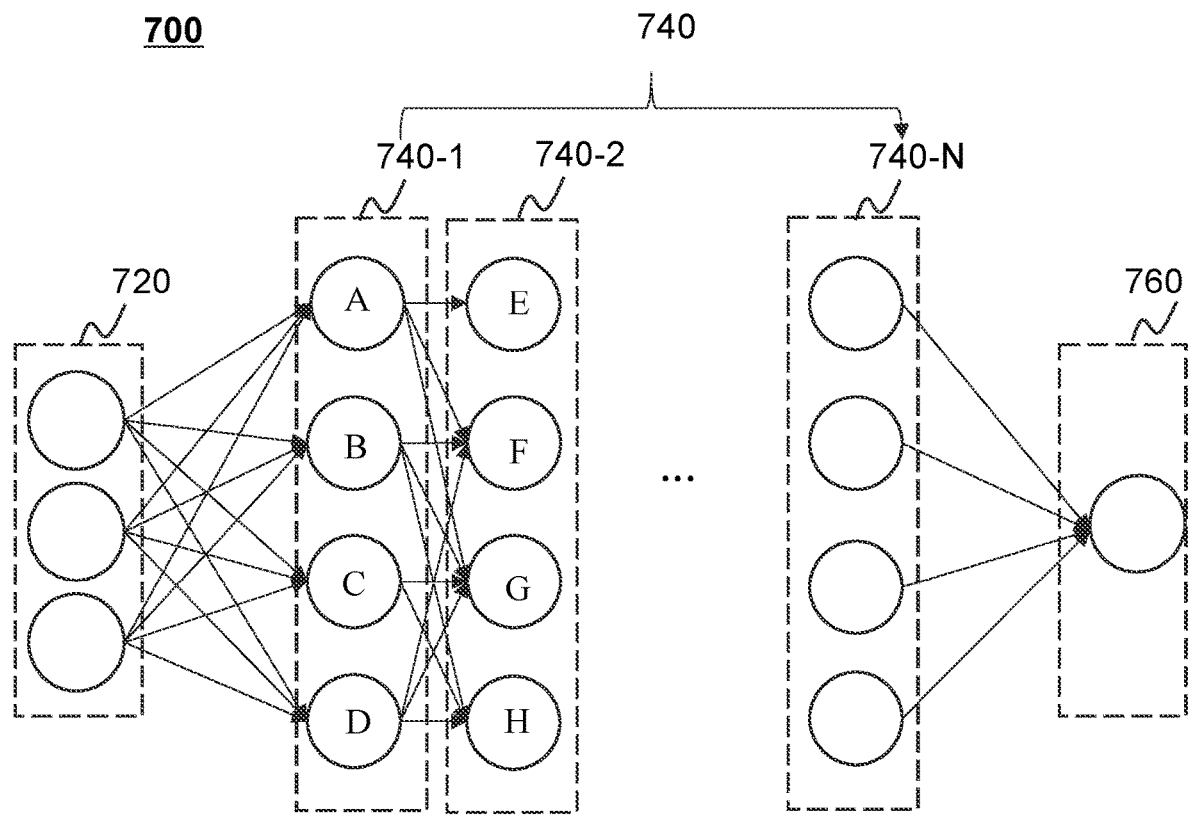
FIG. 7 is a schematic diagram illustrating an exemplary back propagation (BP) neural network model according to some embodiments of the present disclosure.

FIG. 7 is a schematic diagram illustrating an exemplary convolutional neural network (CNN) model according to some embodiments of the present disclosure.

The CNN model 700 may include an input layer 720, hidden layers 740, and an output layer 760. The multiple hidden layers 740 may include one or more convolutional layers, one or more Rectified Linear Units layers (ReLU layers), one or more pooling layers, one or more fully connected layers, or the like, or a combination thereof.

For illustration purposes, exemplary hidden layers 740 of the CNN model, including a convolutional layer 740-1, a pooling layer 740-2, and a fully connected layer 740-N, are illustrated. As described in connection with process 600, the model determination module 406 may acquire a PET image, an MR image, and a reference attenuation correction image associated with the PET image as an input of the CNN model. The PET image and the MR image may be denoted by matrixes including a plurality of elements, respectively. A plurality of elements in a matrix may have a value (also referred to as pixel/voxel value) representing a characteristic of the element. Values of at least one portion of the plurality of elements in the PET image and the MR image may be inputted into the hidden layers 740.

The convolutional layer 740-1 may include a plurality of kernels (e.g., A, B, C, and D). The plurality of kernels may be used to extract a PET image and an MR image of a subject. In some embodiments, each of the plurality of kernels may filter a portion (e.g., a region) of the PET image and corresponding portion of the MR image of the subject to produce a specific feature or area corresponding to the portion (e.g., a region) of the PET image and corresponding portion of the MR image of the subject. The feature may include a low-level feature (e.g., an edge feature, a texture feature), a high-level feature (e.g., a semantic feature), or a complicated feature (e.g., a deep hierarchical feature) that is calculated based on the kernel(s).

The pooling layer 740-2 may take the output of the convolutional layer 740-1 as an input. The pooling layer 740-2 may include a plurality of pooling nodes (e.g., E, F, G, and H). The plurality of pooling nodes may be used to sample the output of the convolutional layer 740-1, and thus may reduce the computational load of data processing and increase the speed of data processing of the imaging system 100. In some embodiments, the model determination module 406 may reduce the volume of the matrix corresponding to a PET image and an MR image in the pooling layer 740-2. For example, the model determination module 406 may divide the PET image and the MR image into multiple regions in the pooling layer 740-2. The average of values of pixels in one of the multiple regions may be designated as the value of a pixel representing the one of the multiple regions.

The fully connected layer 740-N may include a plurality of neurons (e.g., O, P, M, and N). The plurality of neurons may be connected to a plurality of nodes from the previous layer, such as a pooling layer. In the fully connected layer 740-3, the model determination module 406 may determine a plurality of vectors corresponding to the plurality of neurons based on the PET image and MR image and further weigh the plurality of vectors with a plurality of weighting coefficients.

The output layer 760 may determine an output, such as an attenuation correction image, based on the plurality of vectors and weighting coefficients obtained in the fully connected layer 740-N. In some embodiments, the output layer 760 may specify the deviation or difference between a predicted output (e.g., an estimated attenuation correction image associated with the PET image) and a true label (e.g., a reference attenuation correction image associated with the PET image) based on a cost function. The deviation or difference between a predicted output (e.g., an estimated attenuation correction image associated with the PET image) and a true label (e.g., a reference attenuation correction image associated with the PET image) may be defined by a value of the cost function. If the value of the cost function satisfies a condition, the training process of the CNN model may be completed. If the value of the cost function does not satisfy the condition, the parameters of the CNN model may be updated using a gradient descent algorithm. For example, if the predicted output (e.g., a pixel value in an estimated attenuation correction image associated with the PET image) is less than the true label (e.g., a pixel value in a reference attenuation correction image associated with the PET image), one portion of the weightings of the CNN model may be increased. If the predicted output (e.g., a pixel value in an estimated attenuation correction image associated with the PET image) exceeds the true label (e.g., a pixel value in a reference attenuation correction image associated with the PET image), one portion of the weightings of the CNN model may be decreased.

It shall be noted that the CNN model may be modified when applied in different conditions. For example, in a training process, a Rectified Linear Units layer may be added. An activation function may be used by the Rectified Linear Units layer to constrain an output of the Rectified Linear Units layer. Exemplary activation functions may include a linear function, a ramp function, a threshold function, a Sigmoid function, etc.

In some embodiments, the model determination module 406 may get access to multiple processing units, such as GPUs, in the imaging system 100. The multiple processing units may perform parallel processing in some layers of the CNN model. The parallel processing may be performed in such a manner that the calculations of different nodes in a layer of the CNN model may be assigned to two or more processing units. For example, one GPU may run the calculations corresponding to kernels A and B, and the other GPU(s) may run the calculations corresponding to kernels C and D in the convolutional layer 740-1. Similarly, the calculations corresponding to different nodes in another type of layers in the CNN model may be performed in parallel by the multiple GPUs.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A system, comprising:
    at least one storage device storing executable instructions, and
    at least one processor in communication with the at least one storage device, when executing the executable instructions, causing the system to:
        obtain multiple groups of training data, each of the multiple groups of training data including a positron emission tomography (PET) image of a sample, a magnetic resonance (MR) image of the sample, and a reference attenuation correction image corresponding to the PET image and the MR image;
        obtaining a neural network model;
        generate a target neural network model by training the neural network model using the multiple PET images, the multiple MR images, and the multiple reference attenuation correction images in the multiple groups of the training data, wherein the target neural network model provides a mapping relationship between the multiple PET images, the multiple MR images, and the multiple reference attenuation correction images.

2. The system of claim 1, wherein the neural network model includes at least one of a convolutional neural network (CNN) model, a back propagation (BP) neural network model, a radial basis function (RBF) neural network model, a deep belief nets (DBN) neural network model, or an Elman neural network model.

3. The system of claim 1, wherein to obtain multiple groups of training data, the at least one processor is further configured to cause the system to:
    for each of the multiple groups of training data,
        obtain a CT image of the sample; and
        determine the reference attenuation correction image based on the CT image of the sample.

4. The system of claim 3, wherein to determine the reference attenuation correction image based on the CT image of the sample, the at least one processor is further configured to cause the system to:
    determine the reference attenuation correction image by transforming the CT image of the sample using at least one of a scaling technique, an image segmentation technique, a Hybrid technique, a bilinear technique, or a dual-energy X-ray CT technique.

5. The system of claim 1, wherein to obtain multiple groups of training data, the at least one processor is further configured to cause the system to:
for one group of the multiple groups of training data,
determine the reference attenuation correction data based on the MR image or the PET image of the sample corresponding to the reference attenuation correction data.

6. The system of claim 5, wherein to determine the reference attenuation correction data based on the MR image or the PET image of the sample corresponding to the reference attenuation correction data, the at least one processor is further configured to cause the system to:
determine, based on the corresponding MR image or the corresponding PET image, the reference attenuation correction data using at least one of a segmentation technique or a body map technique.

7. The system of claim 1, wherein to generate a target neural network model by training the neural network model using the multiple PET images, the multiple MR images, and the multiple reference attenuation correction images in the multiple groups of the training data, the at least one processor is further configured to cause the system to:
for one group of the multiple groups of training data,
input a PET image and an MR image in the group into the neural network model;
generate an estimated attenuation correction image by processing the PET image and the MR image by the neural network model;
determine a difference between the estimated attenuation correction image and a reference attenuation correction image in the group; and
generate the target neural network model by updating, based on the difference, the neural network model.

8. The system of claim 1, wherein the at least one processor is further configured to cause the system to:
obtain a PET image of a subject acquired by a PET scanner;
obtain an MR image of the subject acquired by an MR scanner; and
generate an attenuation correction image based on the PET image, the MR image and the mapping relationship provided by the target neural network.

9. The system of claim 8, wherein the at least one processor is further configured to cause the system to:
perform a post-processing operation on the attenuation correction data corresponding to the subject, the post-processing operation including at least one of an interpolation operation or a registration operation.

10. The system of claim 8, wherein the at least one processor is further configured to cause the system to:
perform a pre-processing operation on the PET image or the MR image, the pre-processing operation including at least one of a filtering operation, a smoothing operation, a transformation operation, or a denoising operation.

11. A method implemented on a computing device, the computing device including at least one processor and at least one storage device, the method comprising:
obtaining multiple groups of training data, each of the multiple groups of training data including a positron emission tomography (PET) image of a sample, a magnetic resonance (MR) image of the sample, and a reference attenuation correction image corresponding to the PET image and the MR image;
obtaining a neural network model;
generating a target neural network model by training the neural network model using the multiple PET images, the multiple MR images, and the multiple reference attenuation correction images in the multiple groups of the training data, wherein the target neural network model provides a mapping relationship between the multiple PET images, the multiple MR images, and the multiple reference attenuation correction images.

12. The method of claim 11, wherein the neural network model includes at least one of a convolutional neural network (CNN) model, a back propagation (BP) neural network model, a radial basis function (RBF) neural network model, a deep belief nets (DBN) neural network model, or an Elman neural network model.

13. The method of claim 11, wherein the obtaining multiple groups of training data, the at least one processor is further configured to cause the system to:
for each of the multiple groups of training data,
obtaining a CT image of the sample; and
determining the reference attenuation correction image based on the CT image of the sample.

14. The method of claim 13, wherein the determining the reference attenuation correction image based on the CT image of the sample includes:
determining the reference attenuation correction image by transforming the CT image of the sample using at least one of a scaling technique, an image segmentation technique, a Hybrid technique, a bilinear technique, or a dual-energy X-ray CT technique.

15. The method of claim 11, wherein the obtaining multiple groups of training data includes:
for one group of the multiple groups of training data,
determining the reference attenuation correction data based on the MR image or the PET image of the sample corresponding to the reference attenuation correction data.

16. The method of claim 15, wherein the determining the reference attenuation correction data based on the MR image or the PET image of the sample corresponding to the reference attenuation correction data includes:
determining, based on the corresponding MR image or the corresponding PET image, the reference attenuation correction data using at least one of a segmentation technique or a body map technique.

17. The method of claim 11, wherein the generating a target neural network model by training the neural network model using the multiple PET images, the multiple MR images, and the multiple reference attenuation correction images in the multiple groups of the training data includes:
for one group of the multiple groups of training data,
inputting a PET image and an MR image in the group into the neural network model;
generating an estimated attenuation correction image by processing the PET image and the MR image by the neural network model;
determining a difference between the estimated attenuation correction image and a reference attenuation correction image in the group; and
generating the target neural network model by updating, based on the difference, the neural network model.

18. The method of claim 11, further comprising:
obtaining a PET image of a subject acquired by a PET scanner;
obtaining an MR image of the subject acquired by an MR scanner; and generating an attenuation correction image based on the PET image, the MR image and the mapping relationship provided by the target neural network.

19. The method of claim 18, further comprising:
performing a post-processing operation on the attenuation correction data corresponding to the subject, the post-processing operation including at least one of an interpolation operation or a registration operation.

20. A non-transitory computer readable medium, comprising at least one set of instructions for data processing, wherein when executed by one or more processors of a computing device, the at least one set of instructions causes the computing device to perform a method, the method comprising:
  obtaining multiple groups of training data, each of the multiple groups of training data including a positron emission tomography (PET) image of a sample, a magnetic resonance (MR) image of the sample, and a reference attenuation correction image corresponding to the PET image and the MR image;
  obtaining a neural network model;
generating a target neural network model by training the neural network model using the multiple PET images, the multiple MR images, and the multiple reference attenuation correction images in the multiple groups of the training data, wherein the target neural network model provides a mapping relationship between the multiple PET images, the multiple MR images, and the multiple reference attenuation correction images.

* * * * *